United States Patent [19]

Wolcott et al.

[11] Patent Number: 4,999,305

[45] Date of Patent: Mar. 12, 1991

[54] APPARATUS FOR TITRATION FLOW INJECTION ANALYSIS

[76] Inventors: Duane K. Wolcott, 3406 Morning Glory, Baton Rouge, La. 70808; Ernest D. Graves, Jr., 329 Daventry Dr., Baton Rouge, La. 70810; David G. Hunt, 7525 Don Budge Ave., Baton Rouge, La. 70808

[21] Appl. No.: 511,875

[22] Filed: Apr. 19, 1990

Related U.S. Application Data

[63] Continuation of Ser. No. 254,502, Oct. 6, 1988, abandoned, which is a continuation of Ser. No. 932,811, Nov. 19, 1986, Pat. No. 4,798,803, which is a continuation-in-part of Ser. No. 512,797, Jul. 11, 1983, abandoned, which is a continuation-in-part of Ser. No. 753,750, Jul. 10, 1985, abandoned.

[51] Int. Cl.$^5$ .............................................. G01N 35/08
[52] U.S. Cl. ........................................ 436/52; 436/68; 436/163; 422/68.1; 422/74; 422/75
[58] Field of Search ........................... 436/52, 68, 163; 422/68, 74, 75

[56] References Cited

U.S. PATENT DOCUMENTS

| | | | |
|---|---|---|---|
| 3,660,035 | 5/1972 | Marsh | 422/75 |
| 4,002,269 | 1/1977 | Negersmith | 436/68 |
| 4,095,472 | 6/1978 | Mowery, Jr. | 73/864.83 |
| 4,097,921 | 6/1978 | Raffaele | 436/68 |
| 4,265,856 | 5/1981 | Falinower | 422/68 |

Primary Examiner—Robert J. Warden
Assistant Examiner—Lynn Kummert
Attorney, Agent, or Firm—Timothy S. Stevens

[57] ABSTRACT

A method for titration flow injection analysis by introducing a multicomponent sample into a carrier stream which flows into a mixing/sensing cell and titrating with a reactant more than one component of the sample by sensing a plurality of endpoints. The apparatus of the invention includes a stirring means within the mixing/sensing cell which generates helical flow within the cell so that bubbles are not retained in the cell.

5 Claims, 2 Drawing Sheets

APPARATUS FOR TITRATION FLOW INJECTION ANALYSIS

This is a continuation of application Ser. No. 254,502, filed Oct. 6, 1988, now abandoned, which is a continuation of application Ser. No. 932,811, filed Nov. 19, 1986, now U.S. Pat. No. 4,798,803, which is a continuation-in-part of application Ser. No. 512,797, filed July 11, 1983, now abandoned which is a continuation-in-part of Ser. No. 753,750 filed 7/10/85, abandoned.

FIELD OF THE INVENTION

This invention relates to a new apparatus and method for improved flow injection titrimetry analysis.

BACKGROUND OF THE INVENTION

The need for repeatable accurate chemical analysis methods and apparatus is ever increasing. In response to this need, a variety of analyzers have been built. With each new analyzer, the focus has consistently been on the construction of analysis apparatus which increases analysis apparatus capacity and reduces the number of required steps in the analysis process. Flow injection analyzers have been built to meet these needs.

Flow injection analyzers are instruments capable of detecting features of a sample injected into a continuously flowing solution. Flow injection analysis is based on an analysis system capable of forming a reproducible gradient of sample in a reagent flow, detectable as a gradient curve. Measurements carried out on the resultant gradient curve are used to determine the characteristics and components of the sample.

A new area in the field of flow injection analysis is flow injection titrimetry (F.I.T.) which combines the best features of flow injection analysis with titrimetry techniques.

Flow injection titrimetry is derived from titration which is the volumetric determination of a constituent in a known volume of a solution by the slow addition of a standard reacting solution of a known strength until the reaction is completed. Completion of the reaction is frequently indicated by a color change (indicator) or electrochemical change in the solution.

Flow injection titrimetry (F.I.T.) has been developed to produce rapid, simple, reliable, versatile and accurate analysis systems for process control applications. Different from other flow injection analysis techniques, flow injection titrimetry is based on the measurements of peak width rather than peak height. The width of this peak is proportional to the log of the sample concentration. Contrary to other flow injection analysis techniques, flow injection titrimetry makes use of a large sample dispersion to create a concentration gradient over time. This concentration gradient is known as the "exponential concentration gradient". The exponential concentration gradient is the concentration gradient within the mixing cell during flow injection analysis.

The concept of single point titration using flow injection analysis techniques has been described for acid-/base systems by Ove Åstrm's article, "Single-Point Titrations" found in *Analytica Chimica Acta*, 105 (1979) 67-75. The Åstrom method for a single-point titrimetric system for acids and bases utilizes a reaction cell consisting of a reference electrode, a glass electrode, a mixing coil 300 cm long, and teflon injection tubing. Only one analysis can be performed using the reaction cell with detection electrodes. A need has long been felt for a dual analysis system.

Multielement trace analyzers using nonsegmented continuous flow analysis have been described in "Correspondence", *Analytical Chemistry*, Vol. 50, No. 4. (1978) 654-656. However, this analysis technique is taught in only a very general way. The multielement trace analysis using nonsegmented continuous flow for the compounds 4-(2-pyridylazo) resorcinol (PAR), lead (II) and vanadium (V) is colorimetric rather than titrimetric. No specific teaching of multielement trace analysis using flow injection titrimetry has been found, particularly for caustic/carbonate systems.

The apparatus used in multielement trace analysis, generally has included a reaction cell, a measuring instrument, and a recorder or data processing unit, see, "Injection Technique In Dynamic Flow-Through Anaylsis With Electroanalytical Sensors" by Pungor, Feher, Nagy, Toth, Horvai and Gratzl, appearing in *Analytica Chemica Acta*, 109 (1979), 1-24. This apparatus has not been capable of both acting as a reaction cell and a detection cell for multiple endpoint flow injection titrimetry. The present invention seeks to provide such an instrument and an accompanying flow injection titrimetry technique.

Known analysis methods have utilized batch analysis methods for detecting endpoints of independently titratable species in caustic/carbonate reactions. One batch technique, as described in Scotts', *Standard Methods of Chemical Analysis* (5th Ed., p. 2256) describes a double-endpoint determination of sodium hydroxide and sodium carbonate in a mixture thereof by (a) titrating with sulfuric acid to the phenolphthalein endpoint (NaOH converted to $NaHSO_4$ and $H_2O$; $Na_2CO_3$ converted to $NaHCO_3$) and (b) titrating further with sulfuric acid to the methyl-orange endpoint ($NaHCO_3$ converted to $NaHSO_4$, $CO_2$ and $H_2O$). However, batch techniques have numerous drawbacks since they are not capable of continuous quantitative measurements nor continuous titration analysis. The batch titrations must be periodically stopped and the reactors must be cleaned after each reaction is completed. This known technique has required abundant analysis time to obtain the necessary results. A need has existed for determining multiple end points of independently titratable species in a continuous flow, nonbatch type of titration system.

Known continuous flow injection analysis techniques have been developed for continuous flow acid-base titration as described in J. Ruzicka, and E. H. Hansen, *Flow Injection Analysis*, Wiley-Interscience Publication, (Chemical Analysis, Vol. 62), 1981. With the batch tank model developed by Ruzicka et al., the time span between these two observed equivalence points, $t_{eq}$, may be expressed by the following equation:

$$t_{eq} = \frac{V_m}{Q_t} \ln_e C_{so} - \frac{V_m}{Q_t} \ln_e C_t \frac{Q_s}{Q_t} \qquad (1)$$

where $V_m$ is the mixing cell volume which is much larger than the sample volume, $V_s$, $C_{so}$ is the concentration of S in the mixing cell at $t=0$, $Q_s$ is the sample flow rate, and $Q_t$ is the titrant flow rate and thus $$C_{so} = \frac{V_s C_s@}{V_m} \qquad (2)$$

where $C_s@$ is the initial concentration of S. With a single channel manifold as used in this work, $$Q_s = Q_t = Q \qquad (3)$$

and the above equation reduces to $$t_{eq} = \frac{V_m}{Q} \ln_e C_{SO} - \frac{V_m}{Q} \ln_e C_t \qquad (4)$$

where $C_t$ is the concentration of the titrant. Therefore, for the titration of base with an acid $$t_{eq} = \frac{V_m}{Q} \ln_e C_{(base)\,0} - \frac{V_m}{Q} \ln_e nC_{(acid)}. \qquad (5)$$

where n is the number of equivalents weight of the acid. Rearranging this equation and substituting the equation for $C_{so}$, a linear equation is obtained with the form of $$\ln_e C_{base} = K_1 t_{eq} + k_2. \qquad (6)$$

The slope of the response curve is affected by $V_m$ and Q. The intercept, and thus the lower limit of detection, is affected by $V_s$, $V_m$, and $C_{acid}$. Thus if $V_s$ and $V_m$ are kept constant, the sensitivity of the method can be changed by varying Q; and the lower limit of detection can be changed by varying $C_{acid}$. Flow injection titrimetry methods are capable of providing detection limit sensitivities which can be chosen to fit the needs of the analyst.

A problem with the above described single channel system is that the results were limited to the analysis of one component, that is, where $C_s$ is the molar concentration of species to be titrated; K is the constant related to the apparatus including cell volume and flow rate; $t_{eq}$ is the time to an equivalence point, i.e., $t_i$; C is the constant relating concentration of the titrant; $V_m$ is the volume in the mixing cell; and Q is the flow rate then:

$$\ln_e C_s = Kt_{eq} + C \qquad (7)$$

$$C_s = \ln_e^{-1}(Kt_{eq} + C) \qquad (8)$$

$$\ln_e C_s = Q/V_m \, t_{eq} + \ln_e C \qquad (9)$$

Ruzicka and Hansen also developed another titration system, described in "Recent Developments in Flow Injection Analysis: Gradient Techniques and Hydrodynamic Injection", Analytica Chimica Acta, 145 (1983), 1–15. However, this continuous flow multiple endpoint titration system is limited to a teaching for a single component acid-base titration. In particular, the authors focus on the titration of phosphoric acid by $1 \times 10^{-3}$M sodium hydroxide, and do not address a multiple component flow injection analysis multiple endpoint system.

Yet another flow injection titrimetry technique was taught in U.S. Pat. No. 4,283,201 to DeFord et al. In that reference, a titrant is supplied to two parallel fluidly communicating circuits. The first circuit involved a pressure regulator means and a flow restricting means terminating in a first electrical conductivity detection cell means having a vent means. The second circuit involved a flow rate controller means, a sample valve means and a chromatograph column or equivalent means terminating in a second electrical conductivity detection cell means also having a vent means. The electrical output signals representing the electrical conductivity of the fluid conducted through the first cell means and the second cell means were combined in an electrical difference detection means. The electrical output signal generated within the detection means and representative of the difference in the two fluid conductivities was passed to one channel of a dual channel strip chart recording means and additionally passed to an electrical signal derivative detection means. The electrical output signal, representative of the derivative of said difference signal, was then passed to a digital clock and counter means and then to a recording means. The material or sample to be reacted or titrated was supplied to the two parallel fluidly communicating circuits from a third conduit.

The DeFord teaching provided a method and apparatus for flow injection titrimetry which used a plurality of reactant streams, analyzers, and detection apparatus to detect a plurality of end points of a complex sample. This teaching has not satisfied all the needs of the medical, pharmaceutical and argicultural fields in regard to analysis apparatus. A need exists for a flow injection method of analysis which provides data regarding a plurality of end points requiring less equipment and less time than the DeFord teaching. A method and device have long been needed for performing multiple end-point titrations in a single analysis. The present invention seeks to go beyond these teachings and present a method of nonlinear multiple endpoint flow injection titrimetry for several species of sample.

One problem with prior mixing cells for titration flow injection analysis is entrapment of bubbles in the mixing cell. This problem is related to the mixing action of the stirrer in the mixing cell. Bubbles tend to collect on cell walls and to remain in the vortex of the stirred contents of the cell and interfere with analytical accuracy. Special stirrers such as the Fisher Scientific stir bar for spectrophotometer cells, Catalog No. 14-511-72, are designed to minimize aeration and are effective in spectrophotometric cuvettes. They are, however, inadequate in Flow Injection titration analysis because of a demonstrated tendency to form and trap bubbles on the stirrer itself and on the tip of the detector probe. The trapped bubbles interfere with the analytical accuracy. The stirrer of the present invention results in helical flow of the carrier from the inlet to the outlet of the mixing cell with a minimum of vertical mixing (assuming vertical progression of helical flow in the mixing cell). This helical flow, preferably in combination with a chamber which is narrowed near the outlet of the chamber to allow bubble coalescing which facilitates bubble removal from the cell and effectively solves the above mentioned bubble problem.

SUMMARY OF THE INVENTION

The present invention provides a method for determining the titration endpoints of at least two independent titratable species by flow injection analysis of a single sample, comprising the steps of: providing a stream of carrier; introducing a multicomponent sample into the carrier stream; flowing the sample into a mixing and detection cell at a defined carrier flow rate; forming an exponential dilution gradient within the mixing and detection cell; titrating with a reactant, each species of the sample mixture, in the mixing cell, to a plurality of end points; determining the concentration of each species of the sample in the mixing cell by forming a relationship between the time of titrating each species to an equivalence point using the multicomponent system relationship expressed as:

$$T \ln(RF_i) = t_i + T \ln C_t, \quad (10)$$

developed from the equations:

$$t_i = Vm/Q \ln(Vs/Vm) - \ln C_t] + Vm/Q \ln(Sn_iC_i) \quad (11)$$

wherein:
- $t_i$ are the times to titration endpoints;
- $V_s$ is the volume of the sample;
- $V_m$ is the mixed cell volume;
- Q is the flow rate;
- $C_i$ are the molar concentrations of each titratable species in the sample;
- $n_i$ are the number of equivalents of each titratable species in the sample;
- R is the ratio of sample volume to cell volume;
- T is the average cell residence time of titrant;
- $F_i$ are the sample concentration functions corresponding to the relationships between the concentrations of $C_i$, as controlled by the stoichiometry of the species/titrant reactions; and
- $C_t$ is the molar concentration of titrant.

The invention method further comprises the step of using at least two acid base neutralization reactions which occur during the same time interval, during titration of each species of the sample mixture to obtain a plurality of endpoints.

The method invention can be used for the multiple-endpoint titration of the following caustic/carbonate system:

$$n_1 NaOH + n_1 HCL \rightarrow n_1 NaCl + n_1 H_2O \quad (12)$$

$$n_2 Na_2CO_3 + n_2 HCl \rightarrow n_2 NaHCO_3 + n_2 NaCl \quad (13)$$

wherein at $t_1$:
- $n_1$ moles of NaOH = $C_1$, and
- $n_2$ moles of $Na_2CO_3$ = $C_2$ such that:
$F_1 = C_1 + C_2$.

$$n_2 NaHCO_3 + n_2 HCl \rightarrow n_2 NaCl + n_2 CO_2 + n_2 H_2O \quad (14)$$

wherein at $t_2$:
- $n_1$ moles of NaOH = $C_1$
- $n_2$ moles of $Na_2CO_3$ = $C_2$, and
- $n_2$ moles of $NaHCO_3$ is equivalent to the concentration of $C_2$ such that:
$F_2 = C_1 + 2C_2$ to simultaneously determine a plurality of end points.

Alternatively, the method of the invention may further comprise the step of using at least two reduction or oxidation reactions which occur during the same time interval, during titration of each species of the sample mixture to obtain a plurality of endpoints.

The invention yet further involves a mixing cell for titration flow injection analysis, comprising:

a body defining a chamber having a lower inlet port to said chamber and an upper outlet port from said chamber; a sensing means within said chamber placed between said inlet and outlet ports; a stirring means effective to generate helical flow of a liquid flowing into said inlet port to said outlet port in said chamber so that bubbles in said liquid are not retained in said chamber at said detection means.

DETAILED DESCRIPTION OF THE INVENTION

More particularly, the invention achieves a reaction between a sample and a titrant wherein equivalence points are reached such that $$t_1 = Vm/Q[\ln(Vs/Vm) - \ln C_t] + Vm/Q \ln (C_1 + C_2) \quad (15)$$

and $$t_2 = Vm/Q[\ln(Vs/Vm) - \ln C_t] + Vm/Q \ln (C_1 + 2C_2) \quad (16)$$

wherein:
- $t_1$ is the time to the equivalence point of the first species;
- $t_2$ is the time to the equivalence point of the second species;
- $V_s$ is the volume of the sample;
- $V_m$ is the mixed cell volume;
- Q is the flow rate;
- $C_1$ is the molar concentration of the first species; and
- $C_2$ is the molar concentration of the second species.

If a sample plug with concentration $C_s$ is injected into a flowing stream of titrant with concentration $C_t$ and then passed into a mixing cell, and if the mixing and chemical reactions are instantaneous, an exponential concentration gradient is formed. The exponential concentration gradient of the sample and titrant mixture is then passed in the cell to a detector where two or more signal transitions are obtained. These signal transitions are the points at which there is a significant change in the concentration of a monitored species such as pH. The first signal change marks the effective start of the titration. Other signal changes mark the passage of titration equivalent points described by a sudden change in, for example, the carrier pH; and in the case of a single titration species, the end of the titration. Changes in pH may be easily detected with a pH electrode. Other titratable species may be detected using similar sensors (e.g. ion-selective electrodes or amperometric means).

Figure 1:
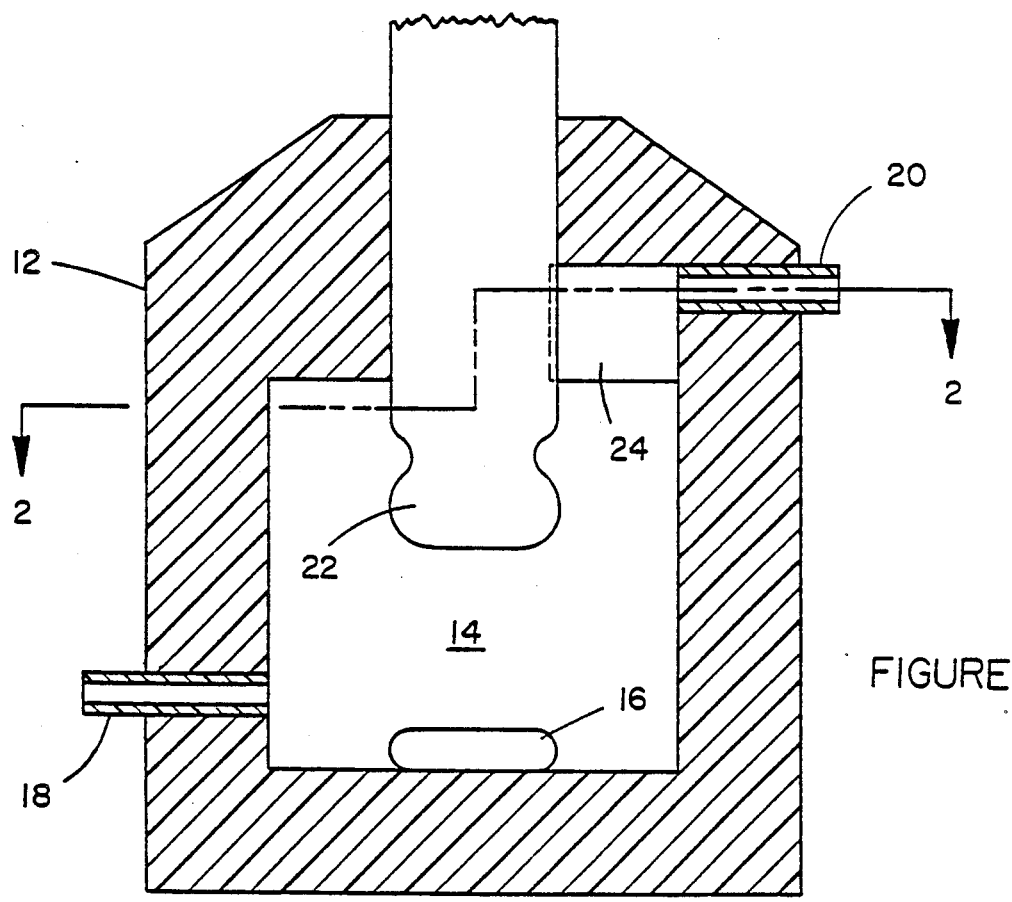
FIG. 1 is a schematic of the preferred embodiment of the apparatus invention.
Figure 2:
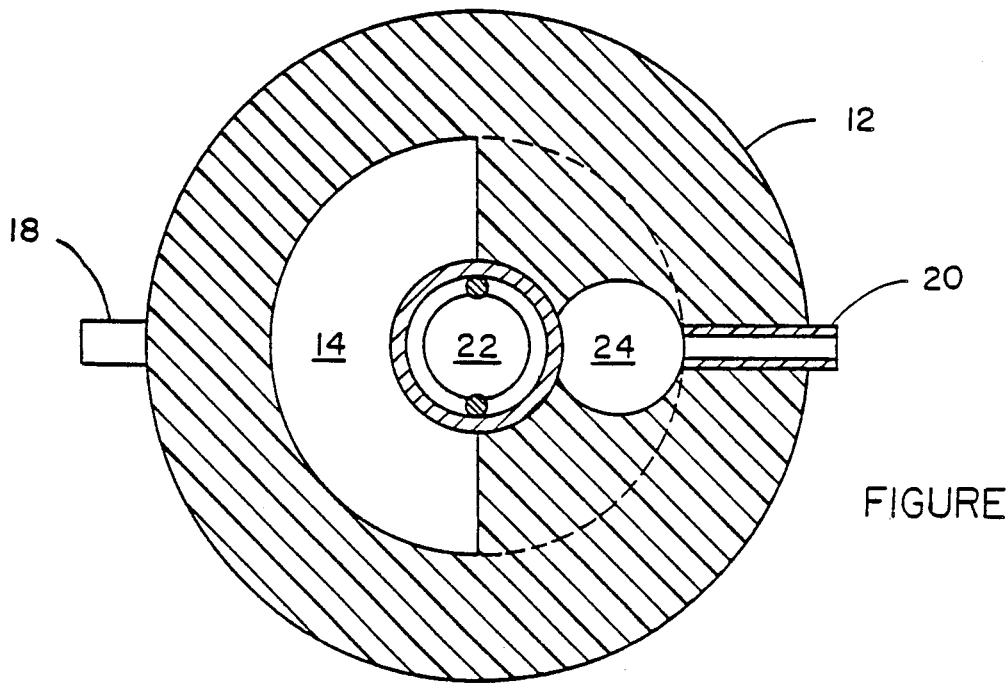
FIG. 2 is a cross section of the embodiment shown in FIG. 1, taken along the cutting line 2—2.

One embodiment of the apparatus invention is shown in FIGS. 1 and 2. The apparatus includes a mixing cell having a body 12 defining a chamber 14. Disposed within the chamber 14 is a stirrer 16. The stirrer 16 serves a dual function within the chamber 14; (1) by mixing the reagent fluid with the sample to promote a reaction and (2) by forcing the fluid to flow in a helical manner upwards through the chamber with a maximum of rotational mixing but with a minimum of up and down mixing so that bubbles do not remain in the chamber 14. A preferred stirrer 16 is a Spinfin type, sold by Ace Scientific, of East Brunswick, N.J., which has been modified by removal of the top fins and addition of side slots 17 (one of which is shown in FIG. 1). Other stirring means, such as devices including stirrers mounted on rotating shafts, may be used as long as they provide for helical flow, and do not trap bubbles.

The body 12 has a lower inlet port 18 and an upper outlet port 20. A sensing means 22 is disposed within the chamber 14. The sensing means can be a pH electrode, an ion specific electrode, or generally any amperometric or potentiometric sensing electrode. A narrowing of the chamber 14 near the outlet port 20 results in a gas trap 24 for trapping bubbles formed during the multiple endpoint titration in the chamber 14. The chamber 14 is designed to provide helical flow between the inlet port 18 and the sensing means 22 whereas the gas trap 24 is designed to provide laminar flow, and collect and dispose of any gas bubbles formed during the reaction. The trap 24 is positioned at the top of chamber 14 near the outlet port 20 to prevent gas bubbles disrupting the titrametric measurements being taken. The outlet port 20 may be positioned from the bottom to the top of the gas trap 24, but is preferably positioned at the top as shown in FIG. 1.

Figure 3:
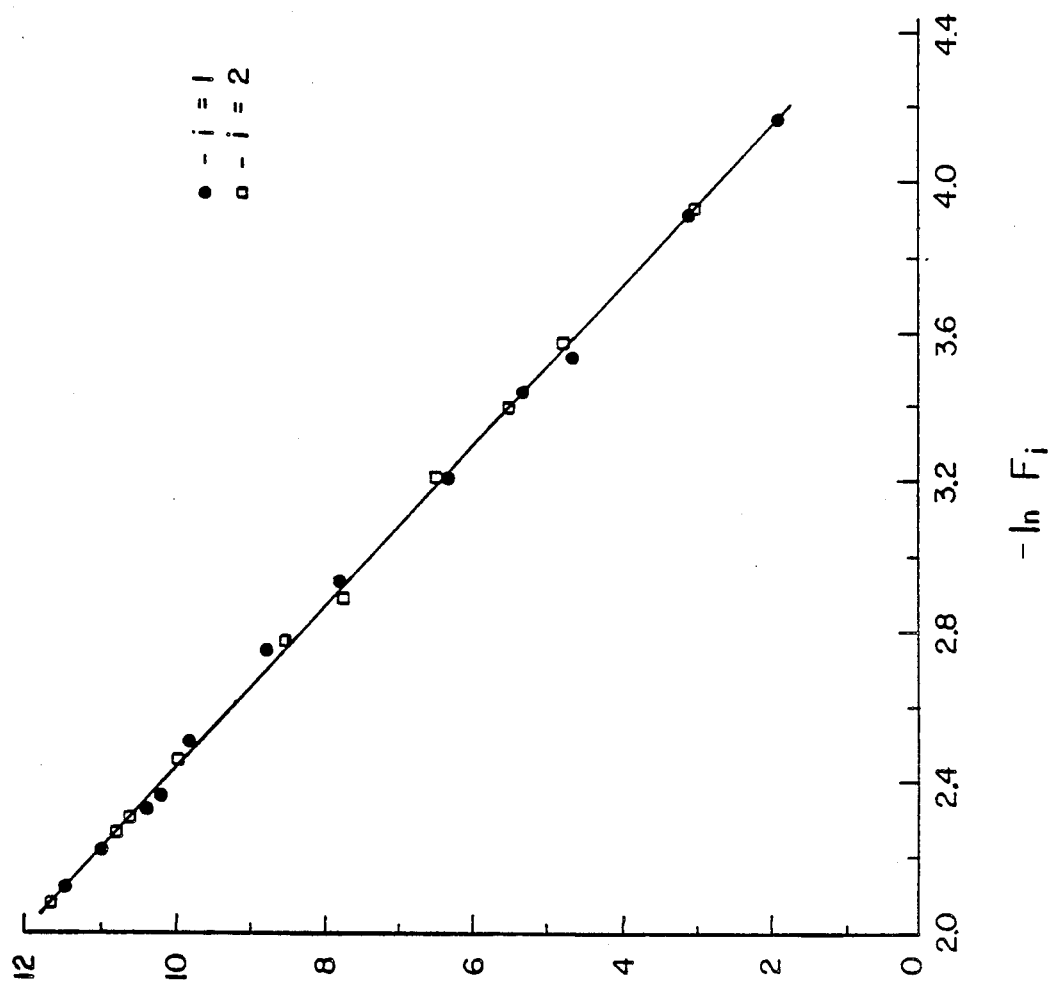
FIG. 3 is a graphic representation of data obtained by the method of the present invention.

Typical results for caustic/carbonate systems using the inventive method and apparatus are depicted in the Table I and in FIG. 3 for the following multicomponent system wherein:
$C_s$ = Sample Concentration
$C_t$ = Titrant Concentration
R = Sample Volume/Cell Volume Ratio
T = Average Cell Residence Time of Titrant
and $$T \ln(RF_i) = t_i + T \ln C_t \quad (17)$$

where:
$t_i$ = Time to equivalence Point i
$F_i$ = Sample Concentration Function
Corresponding to Point i then, for the caustic/carbonate system:

(18)

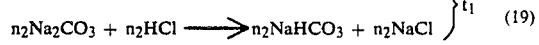
(19)

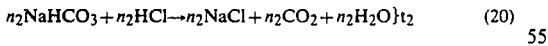
(20)

and for:
Titrated species at time $t_1$:
$n_1$ moles of NaOH (Concentration = $C_1$) and
$n_2$ moles of $Na_2CO_3$ (Concentration = $C_2$)
for a concentration function at $t_1$ of $F_1 = C_1 + C_2$;
and for:
Titrated species at time $t_2$:
$n_1$ moles of NaOH (Concentration = $C_1$) and
$n_2$ moles of $Na_2CO_3$ (Concentration = $C_2$)
for a concentration at $t_2$ of $F_2 = C_1 + 2C_2$;
Equation (17) is rearranged as follows:

$$T \ln R + T \ln F_i = t_i + T \ln C_t \quad (21)$$

$$t_i = T(\ln R - \ln C_t) + T \ln F_i = a + b \ln F_i \quad (22)$$

$$t_1 = a + b \ln(C_1 + C_2) \quad (23)$$

$$t_2 = a + b \ln(C_1 + 2C_2) \quad (24)$$

$$C_1 + C_2 = \ln^{-1}(t_1/b - a/b) = K_1 \quad (25)$$

$$C_1 + 2C_2 = \ln^{-1}(t_2/b - a/b) = K_2 \quad (26)$$

$$C_2 = K_2 - K_1 \quad (27)$$

$$C_1 = K_1 - C_2 = K_1 - (K_2 - K_1) = 2K_1 - K_2 \quad (28)$$

and using system constants which are:
$C_t$ = 0.001 mole/liter
R = 0.0816
Estimated from measurements
T = 4.57 min.
$R = \ln^{-1}(a/b + \ln C_t) = 0.0945$
Calculated from experimental data,
T = b = 4.71 min.
The following example of data was obtained in Table I.

TABLE I

| 100 $C_1$ | 100 $C_2$ | $-\ln F_1$ | $-\ln F_2$ | $t_1$ | $t_2$ | Calculated 100 $C_1$ | 100 $C_2$ |
|---|---|---|---|---|---|---|---|
| 1.2 | 0.3962 | 4.1375 | 3.9158 | 1.875 | 3.063 | 1.124 | 0.453 |
| 1.2 | 0.7925 | 3.9158 | 3.5809 | 3.075 | 4.713 | 1.188 | 0.847 |
| 1.5 | 1.3019 | 3.5749 | 3.1933 | 4.730 | 6.470 | 1.598 | 1.295 |
| 2.6 | 0.3962 | 3.5078 | 3.3836 | 4.563 | 5.375 | 2.266 | 0.526 |
| 2.4 | 0.7925 | 3.4444 | 3.2226 | 5.117 | 6.217 | 2.314 | 0.827 |
| 2.1 | 1.9057 | 3.2175 | 2.8283 | 6.063 | 7.713 | 2.227 | 1.613 |
| 8.8 | 0.6038 | 2.3641 | 2.3018 | 10.016 | 10.392 | 8.157 | 0.740 |
| 8.7 | 0.8962 | 2.3438 | 2.2545 | 10.225 | 10.706 | 8.300 | 1.001 |
| 9.0 | 1.8019 | 2.2254 | 2.0712 | 10.983 | 11.683 | 9.175 | 1.753 |
| 3.6 | 4.3962 | 2.5262 | 2.0881 | 9.767 | 11.650 | 4.286 | 4.153 |
| 4.6 | 0.8019 | 2.9184 | 2.7800 | 7.750 | 8.467 | 4.592 | 0.905 |
| 4.4 | 2.0000 | 2.7489 | 2.4769 | 8.763 | 10.050 | 4.672 | 2.145 |

Where concentration $C_i$ is mole/liter and time $t_i$ is minutes.

The linear relationship of this multiple endpoint system is graphically depicted in FIG. 3.

Statement of Intent

The inventor hereby states his intent to rely on the Doctrine of Equivalents to determine and assess the fair scope of his invention as set out and defined in the following claims.

What is claimed is:
1. A mixing cell comprising:
    (a) a body defining a chamber having a means for introduction of solution to said chamber and a means for exciting of solution from said chamber where introduction of said solution takes place in the chamber at a lower level than exit of said solution;
    (b) a sensing means positioned to be in contact with said solution in said chamber;
    (c) a modified Spinfin TM type stirrer positioned in said chamber, said stirrer modified by removal of top fins and addition of side slots.
2. The mixing cell of claim 1 wherein said chamber narrows near the solution exit region to facilitate the removal of bubbles.
3. The mixing cell of claim 1 wherein said chamber has a fixed volume.
4. The mixing cell of claim 1 wherein said sensing means is a potentiometric electrode.
5. The mixing cell of claim 1 wherein said sensing means is an amperometric electrode.

* * * * *